(12) United States Patent
Creswell et al.

(10) Patent No.: US 11,899,922 B2
(45) Date of Patent: Feb. 13, 2024

(54) SYSTEM, METHOD, AND DEVICE FOR INTERACTIVE NEUROLOGICAL TRAINING

(71) Applicant: Carnegie Mellon University, Pittsburgh, PA (US)

(72) Inventors: David Creswell, Pittsburgh, PA (US); Mathew Polowitz, Pittsburgh, PA (US); Julianna Raye, Los Angeles, CA (US)

(73) Assignee: Carnegie Mellon University, Pittsburgh, PA (US)

( * ) Notice: Subject to any disclaimer, the term of this patent is extended or adjusted under 35 U.S.C. 154(b) by 7 days.

(21) Appl. No.: 17/875,501

(22) Filed: Jul. 28, 2022

(65) Prior Publication Data

US 2023/0033246 A1    Feb. 2, 2023

Related U.S. Application Data

(60) Provisional application No. 63/226,025, filed on Jul. 27, 2021.

(51) Int. Cl.
*G06F 3/0488* (2022.01)
*G10L 25/30* (2013.01)

(52) U.S. Cl.
CPC ............ *G06F 3/0488* (2013.01); *G10L 25/30* (2013.01)

(58) Field of Classification Search
CPC ................................ G06F 3/0488; G10L 25/30
See application file for complete search history.

(56) References Cited

U.S. PATENT DOCUMENTS

| | | | | |
|---|---|---|---|---|
| 9,280,610 | B2 * | 3/2016 | Gruber | G06F 16/9535 |
| 10,331,402 | B1 * | 6/2019 | Spector | G10L 15/1815 |
| 11,030,294 | B2 * | 6/2021 | Huang | G06N 3/063 |
| 2007/0130112 | A1 * | 6/2007 | Lin | G06F 16/41 |
| 2017/0316774 | A1 * | 11/2017 | Sharifi | G10L 13/00 |
| 2019/0043239 | A1 * | 2/2019 | Goel | G06T 13/205 |
| 2020/0175992 | A1 * | 6/2020 | Karnati | G10L 15/22 |
| 2020/0242146 | A1 * | 7/2020 | Kalukin | G06F 16/3329 |
| 2020/0405213 | A1 * | 12/2020 | Chappell, III | G16H 50/30 |
| 2021/0150925 | A1 * | 5/2021 | Birchfield | G09B 5/00 |

* cited by examiner

*Primary Examiner* — Seth A Silverman
(74) *Attorney, Agent, or Firm* — The Webb Law Firm (57) ABSTRACT

Provided are systems, methods, and devices for interactive neurological training. The method includes traversing a graph data structure based on a user profile for a user operating a device, the graph data structure including a plurality of nodes, each node of the plurality of nodes associated with at least one of a logical statement and an audible output, presenting at least one audible output to the user based on at least one node of the graph data structure, receiving a gesture input from the user through the device in response to the at least one audible output, determining a next node of the graph data structure from at least two different nodes connected to the at least one node, and presenting at least one further audible output to the user based on the next node of the graph data structure.

17 Claims, 7 Drawing Sheets

SYSTEM, METHOD, AND DEVICE FOR INTERACTIVE NEUROLOGICAL TRAINING

CROSS-REFERENCE TO RELATED APPLICATION

This application claims priority to U.S. Provisional Patent Application No. 63/226,025, filed Jul. 27, 2021, the disclosure of which is hereby incorporated by reference in its entirety.

BACKGROUND

1. Field

The technology of the disclosure relates generally to neurological training and, in non-limiting embodiments, to systems, methods, and devices for interactive neurological training.

2. Technical Considerations

Existing meditation and therapeutic applications that are executed by mobile devices are functionally linear, and involve playing a pre-recorded audio from start to finish without user interaction. Moreover, mobile applications that capture user feedback require a user to interact with graphical user interfaces (GUIs) in a manner that would disrupt a meditation and/or therapeutic session.

SUMMARY

According to non-limiting embodiments or aspects, provided is a computer-implemented method for interactive neurological training, comprising: traversing, with at least one processor, a graph data structure based on a user profile for a user operating a device, the graph data structure comprising a plurality of nodes, each node of the plurality of nodes associated with at least one of a logical statement and an audible output; presenting at least one audible output to the user based on at least one node of the graph data structure; receiving a gesture input from the user through the device in response to the at least one audible output, the gesture input detected by at least one sensor arranged in the device; determining, based on the gesture input and at least one logical statement associated with the at least one node, a next node of the graph data structure from at least two different nodes connected to the at least one node; and presenting at least one further audible output to the user based on the next node of the graph data structure.

In non-limiting embodiments or aspects, the at least one sensor comprises a touchscreen, and the gesture input comprises at least one press on the touchscreen. In non-limiting embodiments or aspects, the at least one logical statement associated with the at least one node is configured to identify the next node based on the gesture input. In non-limiting embodiments or aspects, the method further includes assigning weights to nodes of the graph data structure based on the user profile. In non-limiting embodiments or aspects, the method further includes traversing the graph data structure based on at least one machine-learning algorithm. In non-limiting embodiments or aspects, the method further includes training the machine-learning algorithm based on the gesture input. In non-limiting embodiments or aspects, the at least one logical statement is configured to identify a node or branch of the graph data structure based on a plurality of different gesture inputs, and the gesture input is selected from the plurality of different gesture inputs. In non-limiting embodiments or aspects, the method further includes: determining if the gesture input was received within a predetermined time period from the at least one audible output; and in response to determining that the gesture input was received within the predetermined time period, determining the next node.

According to non-limiting embodiments or aspects, provided is a system for interactive neurological training, comprising: at least one data storage device comprising at least one graph data structure; and at least one processor in communication with the at least one data storage device, the at least one processor programmed or configured to: traverse a graph data structure from the at least one graphic data structure based on a user profile for a user operating a device, the graph data structure comprising a plurality of nodes, each node of the plurality of nodes associated with at least one of a logical statement and an audible output; present at least one audible output to the user based on at least one node of the graph data structure; receive a gesture input from the user through the device in response to the at least one audible output, the gesture input detected by at least one sensor arranged in the device; determine, based on the gesture input and at least one logical statement associated with the at least one node, a next node of the graph data structure from at least two different nodes connected to the at least one node; and present at least one further audible output to the user based on the next node of the graph data structure.

In non-limiting embodiments or aspects, the at least one sensor comprises a touchscreen, and the gesture input comprises at least one press on the touchscreen. In non-limiting embodiments or aspects, the at least one logical statement associated with the at least one node is configured to identify the next node based on the gesture input. In non-limiting embodiments or aspects, the at least one processor is further configured to assign weights to nodes of the graph data structure based on the user profile. In non-limiting embodiments or aspects, the at least one processor is further configured to traverse the graph data structure based on at least one machine-learning algorithm. In non-limiting embodiments or aspects, the at least one processor is further configured to train the machine-learning algorithm based on the gesture input. In non-limiting embodiments or aspects, the at least one logical statement is configured to identify a node or branch of the graph data structure based on a plurality of different gesture inputs, and the gesture input is selected from the plurality of different gesture inputs. In non-limiting embodiments or aspects, the at least one processor is further configured to: determine if the gesture input was received within a predetermined time period from the at least one audible output; and in response to determining that the gesture input was received within the predetermined time period, determine the next node.

According to non-limiting embodiments or aspects, provided is a computer program product for interactive neurological training, comprising at least one computer-readable medium including program instructions that, when executed by at least one processor, cause the at least one processor to: traverse a graph data structure based on a user profile for a user operating a device, the graph data structure comprising a plurality of nodes, each node of the plurality of nodes associated with at least one of a logical statement and an audible output; present at least one audible output to the user based on at least one node of the graph data structure; receive a gesture input from the user through the device in response to the at least one audible output, the gesture input detected by at least one sensor arranged in the device; determine, based on the gesture input and at least one logical statement associated with the at least one node, a next node of the graph data structure from at least two different nodes connected to the at least one node; and present at least one further audible output to the user based on the next node of the graph data structure.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying figures, in which.

DETAILED DESCRIPTION

It is to be understood that the embodiments may assume various alternative variations and step sequences, except where expressly specified to the contrary. It is also to be understood that the specific devices and processes described in the following specification are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include a GPU, a CPU, a processor, a microprocessor, a controller, a microcontroller, and/or the like. In non-limiting embodiments, a computing device may be comprised of a plurality of circuits.

As used herein, the term "communication" may refer to the reception, receipt, transmission, transfer, provision, and/or the like, of data (e.g., information, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

In non-limiting embodiments, provided is a system for providing an interactive neurological training session to a user operating a mobile device, such as a mobile phone, tablet computer, wearable device, and/or the like, executing a mobile application or accessing a remote application. As used herein, the term "interactive neurological training" refers to a process in which user guidance (e.g., audio playback), user responses, and program logic are used to train (e.g., stimulate, invigorate, relax, improve, etc.) a user's cognitive functioning and cognitive response patterns. For example, an interactive neurological training session may include an audible and bidirectional therapy session configured to improve a user's mental health, wellbeing, and cognitive functioning from a therapeutic and/or physiological perspective. An interactive neurological training session may include, for example, a guided therapy and/or meditation session in which a user is guided through a neurological training program (e.g., such as a lesson) with audible instructions configured to optimize neurological activity in the user through physiological traits such as concentration, stressor reactivity, and/or the like. Through a combination of audio playback, user responses, and program logic, non-limiting embodiments may aid in training and neurologically optimizing a user's cognitive functioning and cognitive response patterns through meditation, relaxation, concentration, and/or the like.

Non-limiting embodiments provide for a dynamic training session that varies for each user and/or in each instance based on user input received throughout the session and in response to one or more instructions. In this manner, a user may influence a path of the session without opening their eyes and/or disrupting their state of mind. The user's input may be used to train a machine-learning model to improve the neurological training program and/or other neurological training programs (e.g., such as subsequent lessons) for that particular user and/or similar users. Non-limiting embodiments provide for a customized, dynamic neurological training experience that may reduce the amount of audio played for a user by eliminating unnecessary audio, thereby reducing the use of computational resources and/or network bandwidth.

Figure 1:
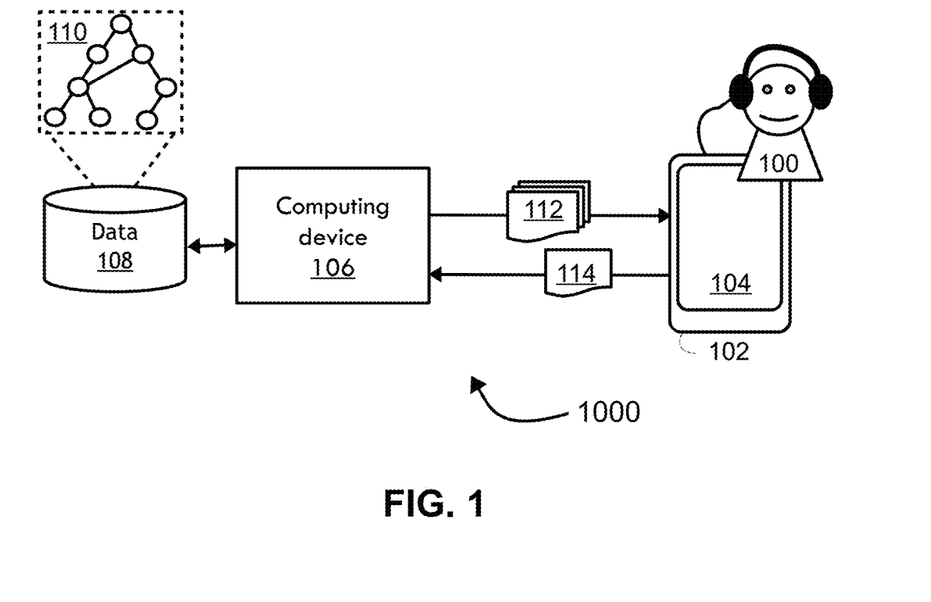
FIG. 1 illustrates a system for interactive neurological training according to non-limiting embodiments or aspects.

Referring now to FIG. 1, a system 1000 for interactive neurological training is shown according to non-limiting embodiments or aspects. The system 1000 includes a computing device 106, such as a server computer, in communication with a mobile device 102 operated by a user 100. The computing device 106 is in communication with a data storage device 108 that includes one or more models 110. In non-limiting embodiments, the models may include graph data structures having connected nodes. In operation, the user 100 operates the mobile phone and receives instructions via audio and/or a GUI displayed on a touchscreen 104 of the mobile device 102. The computing device 106 may provide instructions 112 to the mobile device based on traversing a model 110 and receive a response signal 114 from the mobile device 102.

For example, the instructions 112 may cause one or more audio clips to be output by the mobile device 102. The user 100 may respond to the instructions 112 by interacting with the mobile device 102. For example, the user 100 may tap the touchscreen 104 of the mobile device 102 in response to an instruction 112, which causes a response signal 114 to be generated by the mobile device 102 and communicated back to the computing device 106. The response signal 114 may include, for example, a message or other indication transmitted during a communication session between the mobile device 102 and computing device 106. The response signal 114 may be used by the computing device to obtain a next instruction from the model 110 and communicate that next instruction to the mobile device 102. For example, the computing device 114 may process logic associated with a current node of the model 110 based on the response signal 114 to determine the next node of the model 110 and the instructions that correspond to the next node.

In non-limiting embodiments, the mobile device 102 may be configured (e.g., through an application executing thereon) to generate a response signal 114 based on the user 100 touching anywhere on the touchscreen 104. In this manner, the user 100 may interact with the system 1000 while the user's eyes are closed. This permits the user 100 to listen to the instructions via audio and respond to the instructions without opening their eyes or concentrating on tapping a particular portion of the touchscreen 104. In non-limiting embodiments, all inputs received through the touchscreen (e.g., any type of gesture input on the touchscreen, such as a tap, swipe, or the like) while the user is being instructed (e.g., during a "guided instruction mode") may be translated to a singular input regardless of where the user taps (e.g., if the user taps on a button or other selectable option on the GUI). In this manner, the application may treat touchscreen inputs differently while in the application is an active mode (e.g., a "guided instruction mode") than when in a non-active mode (e.g., a "browsing mode").

In non-limiting embodiments, other user inputs that do not require the user 100 to look at the mobile device 102 may be used additionally or alternatively to touchscreen inputs to generate a response signal 114. For example, non-limiting embodiments may generate response signals 114 based on inertial inputs (e.g., tilting, shaking, and/or moving the device) detected with sensors in the mobile device 102 (e.g., accelerometer, gyroscope, compass, camera, and/or the like), audio inputs (e.g., based on the user 100 speaking or making noises) detected with a microphone in the mobile device 102, and/or other tactile inputs detected with physical buttons, fingerprint readers, and/or the like.

In non-limiting embodiments, the response signal 114 may indicate one of a plurality of possible options. For example, a user 100 may be prompted to provide one tap on the touchscreen 104 for a first response and two taps on the touchscreen 104 for a second response. It will be appreciated that any number of different responses and combinations of inputs may be used. In this manner, a user 100 may answer an inquiry that affects the path (e.g., the next node of the model 110) of the session. Branching logic of the model 110 may guide a user down one of multiple different paths at one or more nodes of a graph data structure based on the response signal 114 (e.g., one tap, two taps, or some other input). In some non-limiting embodiments, a binary choice may be made by tapping or not tapping, or a single tap or a double tap. In some non-limiting embodiments, third and/or further tabs or other inputs may be used to select from multiple options.

In non-limiting embodiments, the mobile device 102 may be configured to operate independent of computing device 106. For example, the mobile device 102 may include one or more applications stored on memory local to the mobile device 102 (e.g., internal memory) configured to conduct an interactive neurological training session with the user 100 without a network connection. In such an example, the instructions 112 may be provided by an application or service local to the mobile device 102 and the data storage device 108 may also be local to the mobile device 102. Accordingly, non-limiting embodiments may operate local on the mobile device 102 and may not include a remote server such as computing device 106. In non-limiting embodiments, the mobile device 102 may communicate with the computing device 106 periodically to download updates, provide usage data, and/or the like.

Figure 2:
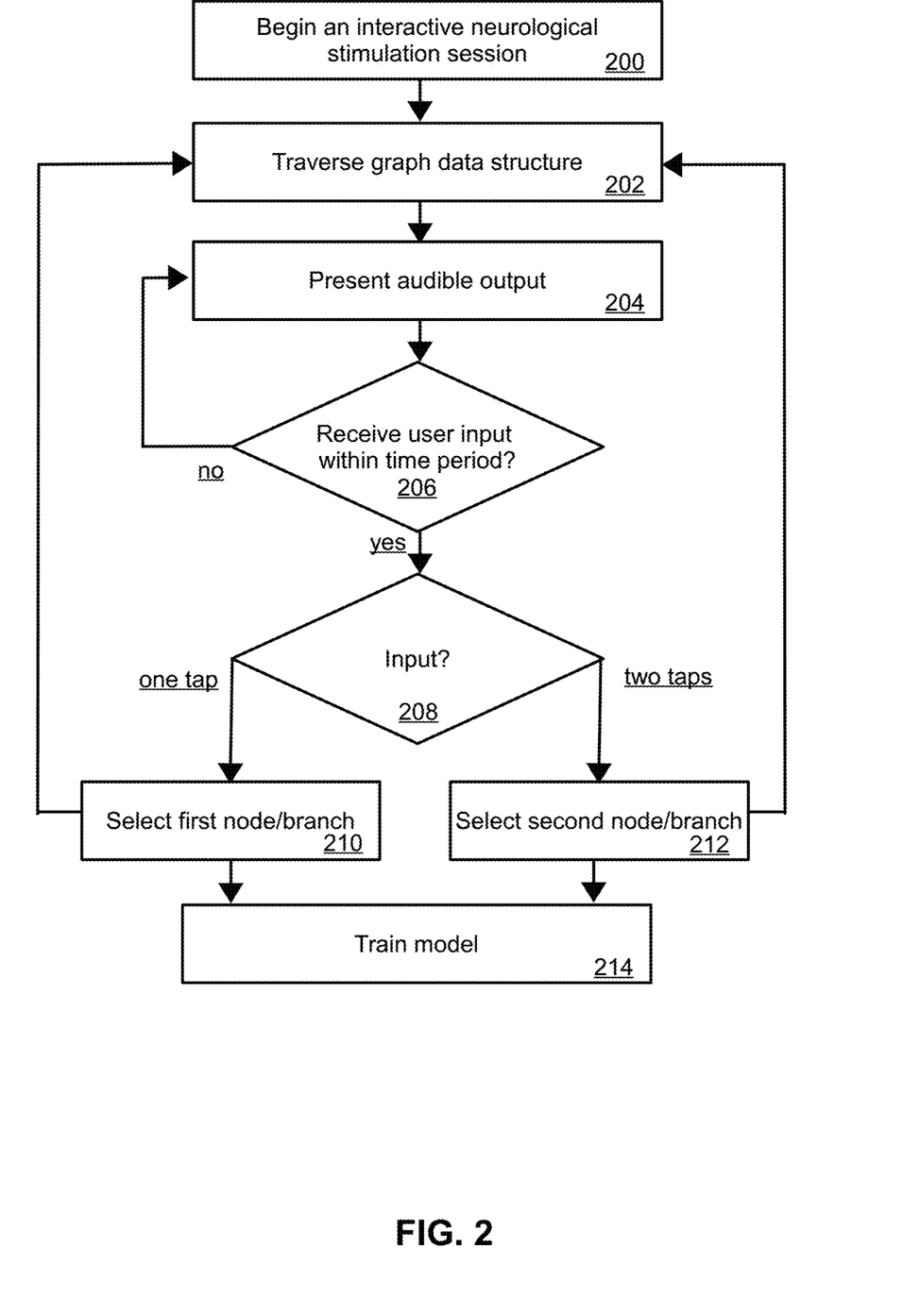
FIG. 2 illustrates a flow diagram for a method of compensating for drift of an inertial sensor according to non-limiting embodiments or aspects.

Referring now to FIG. 2, a flow diagram for a method for interactive neurological training is shown according to non-limiting embodiments or aspects. The steps shown in FIG. 2 are for example purposes only, and it will be appreciated that additional, fewer, different, and/or a different order of steps may be used in non-limiting embodiments. At a first step 200, an interactive neurological training session may begin. For example, an application executing on the mobile device may engage the user by communicating one or more instructions. Initial instructions may be visual and/or audible, and may provide general information to the user about the interactive neurological training session. For example, initial instructions may prompt the user to use headphones, adjust the volume, and/or the like. In non-limiting embodiments, a user may select from multiple different interactive neurological training programs (e.g., mediation lessons). In some examples, an interactive neurological training program may be automatically selected based on the user's progress, user profile, and/or the like. In non-limiting embodiments, a user may log in to the application with credentials, such as a user name, password, biometric, and/or the like.

At step 202 of FIG. 2, a graph data structure is traversed. For example, an interactive neurological training model may include a graph data structure with a plurality of nodes connected in a plurality of paths. Each node of the graph data structure may be associated with one or more instructions and/or branching logic (e.g., one or more rules to determine a next node for traversal). At step 204, an audible output is presented to the user. For example, an audio file or text-to-speech synthesis may be played to the user based on a current node of the graph data structure. The audible output may instruct the user to provide an input (e.g., tap once for a first option, tap twice for a second option, etc.). For example, audio may be played that asks during a session "Was that experience neutral, relaxing, or pleasant in some other way? Or did you find yourself agitated, impatient, preoccupied, or uncomfortable? If it was more pleasant, tap once. If it was more unpleasant, tap twice." Other questions may include, as an example, asking the user if the need to hear instructions again, if they are doing well, if they would like to go "deep", if the experience was restful, if the experience was pleasant, and/or if they need additional guidance or support because they are distracted, agitated, sleepy, or the like.

At step 206 it is determined whether a user input is received within a time period. For example, a predetermined time period (e.g., 30 seconds) may begin upon the audible output being presented at step 204. A programmatic timer may be incremented until reaching a maximum value. If user input is not received before expiration of the time period, the method may proceed back to step 204 and the audible output may be presented again. Alternatively, the absence of an input at step 206 may cause the method to assume or infer an input and continue (e.g., skipping to steps 210 or 212).

With continued reference to FIG. 2, if an input is received within the time period at step 206, the method may continue to step 208 in which the type of input is determined. For example, at step 208 it may be determined if the input is one tap on the touchscreen, two taps on the touchscreen, or another input. In the example depicted in FIG. 2, if one tap is detected the method may proceed to step 210 in which a first node (identifying a first branch that will be traversed) is selected. If two taps are detected, the method may proceed to step 212 in which a second node (identifying a second branch that will be traversed) is selected. It will be appreciated that any number of inputs may be used to select between any number of nodes and associated branches of the graph data structure. In non-limiting embodiments in which only a single option is available, this step 208 may be skipped and the method may proceed to step 210 and/or step 212 depending on the logic. Once a next node is selected, the method may proceed back to step 202.

At step 214 of FIG. 2, the interactive neurological training model may be trained based on one or more user inputs and/or other data collected during the interactive neurological training session. For example, weights of different nodes in a graph data structure may be increased or decreased to affect how it is traversed in future iterations. In some examples, a different graph data structure (e.g., for a subsequent or more advanced session) may be modified based on training the neurological training model. Although step 214 is shown in FIG. 2 as being subsequent to steps 210 and 212, it will be appreciated that training the interactive neurological training model may occur at any time, such as after a session is completed.

Figure 3A:
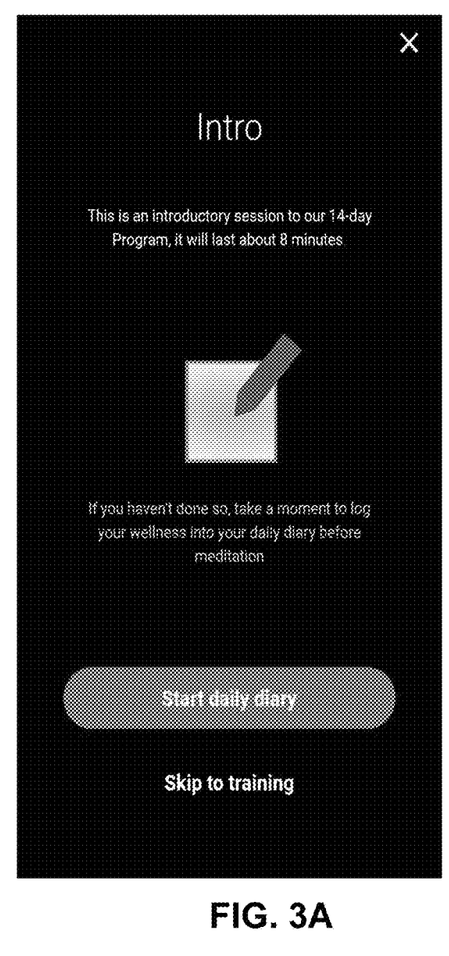
FIGS. 3A-3C illustrate graphical user interfaces for a neurological training program according to non-limiting embodiments or aspects.
Figure 3B:
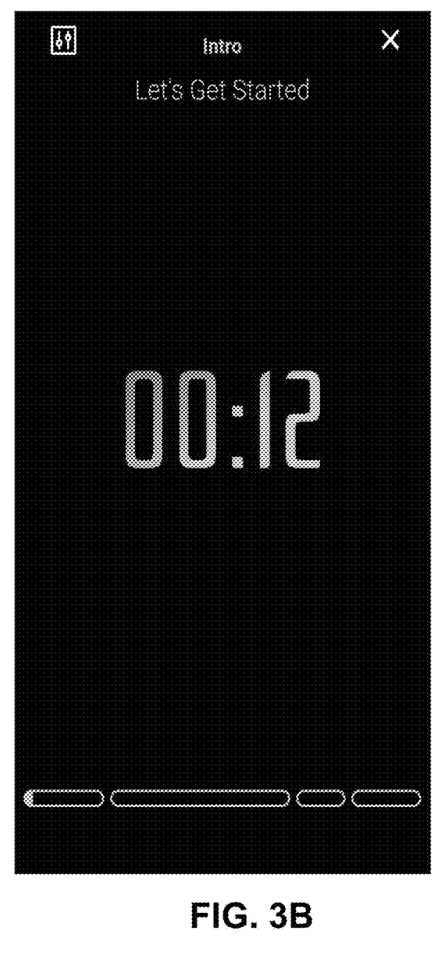
Figure 3C:
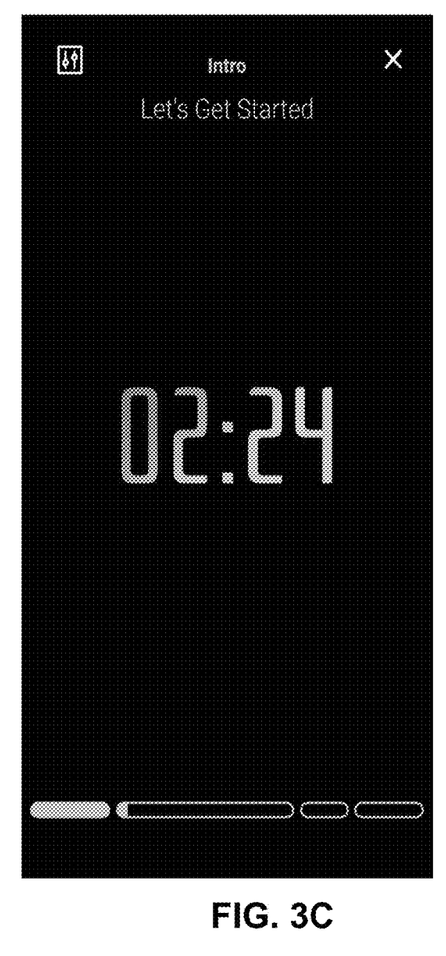

Referring now to FIGS. 3A-3C, GUIs are shown for a neurological training program according to non-limiting embodiments. As shown, an initial program GUI 3A may provide a user with options to create a log (e.g., a diary) or to "skip to training" (begin a lesson, such as a neurological training lesson). FIG. 3B shows a GUI with a timer and a progress bar. In non-limiting embodiments, and as shown in the example of FIG. 3B, the progress bar may include multiple segments that represent different portions of a neurological training program. These portions may change based on user input (e.g., tapping the screen) received during a prior portion. For example, the first portion being played to a user in FIG. 3B may prompt the user to provide one input (e.g., a single tap) if they have experience with meditation or therapy, or a second input (e.g., a double tap) if they do not have experience with meditation or therapy. In response to the user input, the second portion of the progress bar (actively playing audio in FIG. 3C) may represent a different portion of audio depending on the user input.

Figure 4A:
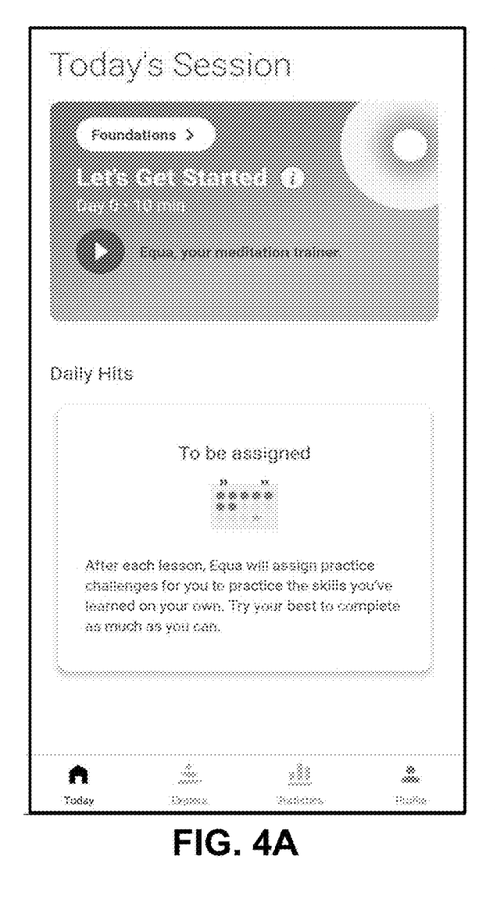
FIGS. 4A-4C illustrate graphical user interfaces for a system for neurological training according to non-limiting embodiments or aspects.
Figure 4B:
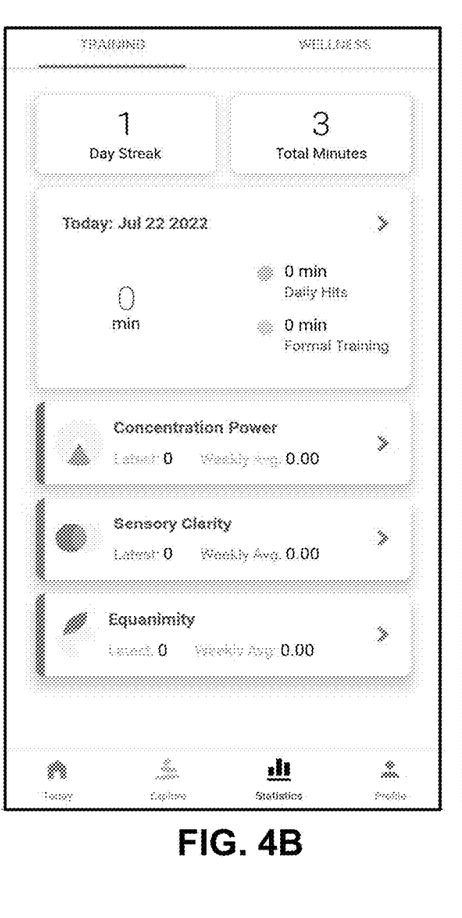
Figure 4C:
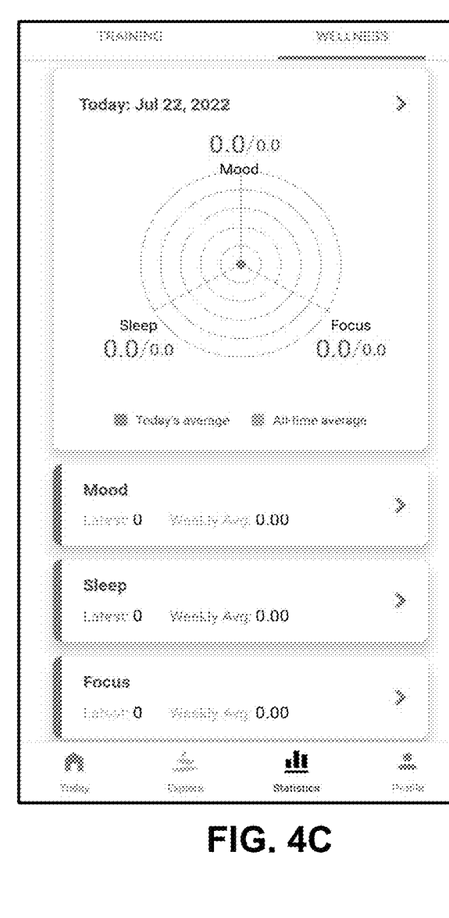

Referring now to FIGS. 4A-4C, GUIs are shown for a system for neurological training according to non-limiting embodiments. FIG. 4A illustrates a landing GUI that may be displayed to a user upon opening a mobile application that shows a suggested neurological training program (e.g., such as a lesson) and one or more tasks for the user to complete (e.g., such as homework assigned after a lesson is completed). FIG. 4B illustrates a training dashboard GUI that shows user profile and statistical information. For example, the number of consecutive days the application is used, the total amount of time spent with the application, and various other metrics (concentration power, sensory clarity, and equanimity) may be displayed. FIG. 4C illustrates a wellness dashboard GUI that shows metrics about the user derived from data collected during sessions, responses to queries (e.g., from the queries shown and described in connection with FIGS. 5A and 5B), and/or from other sources (e.g., user profile information, health or fitness applications, external databases, and/or the like). In some non-limiting embodiments, responses to queries may be collected daily or at other intervals and used to determine and display a user's progress over time.

In non-limiting embodiments, metrics such as concentration power, sensory clarity, and equanimity may be a focus of one or more neurological simulation programs. In non-limiting embodiments, each neurological simulation program may be configured to train for and optimize one or more such metrics. The metrics may correspond to life outcomes, such as mood, sleep, and focus. In non-limiting embodiments, the metrics may be generated from data collected during sessions and/or from other sources (e.g., user profile information, health or fitness applications, and/or the like) in addition to user responses to queries about outcomes. For example, before and/or after a session, a user may be prompted to provide one or more responses to questions that ask about mood, sleep patterns, focus, and/or other mental/physiological characteristics.

Figure 5A:
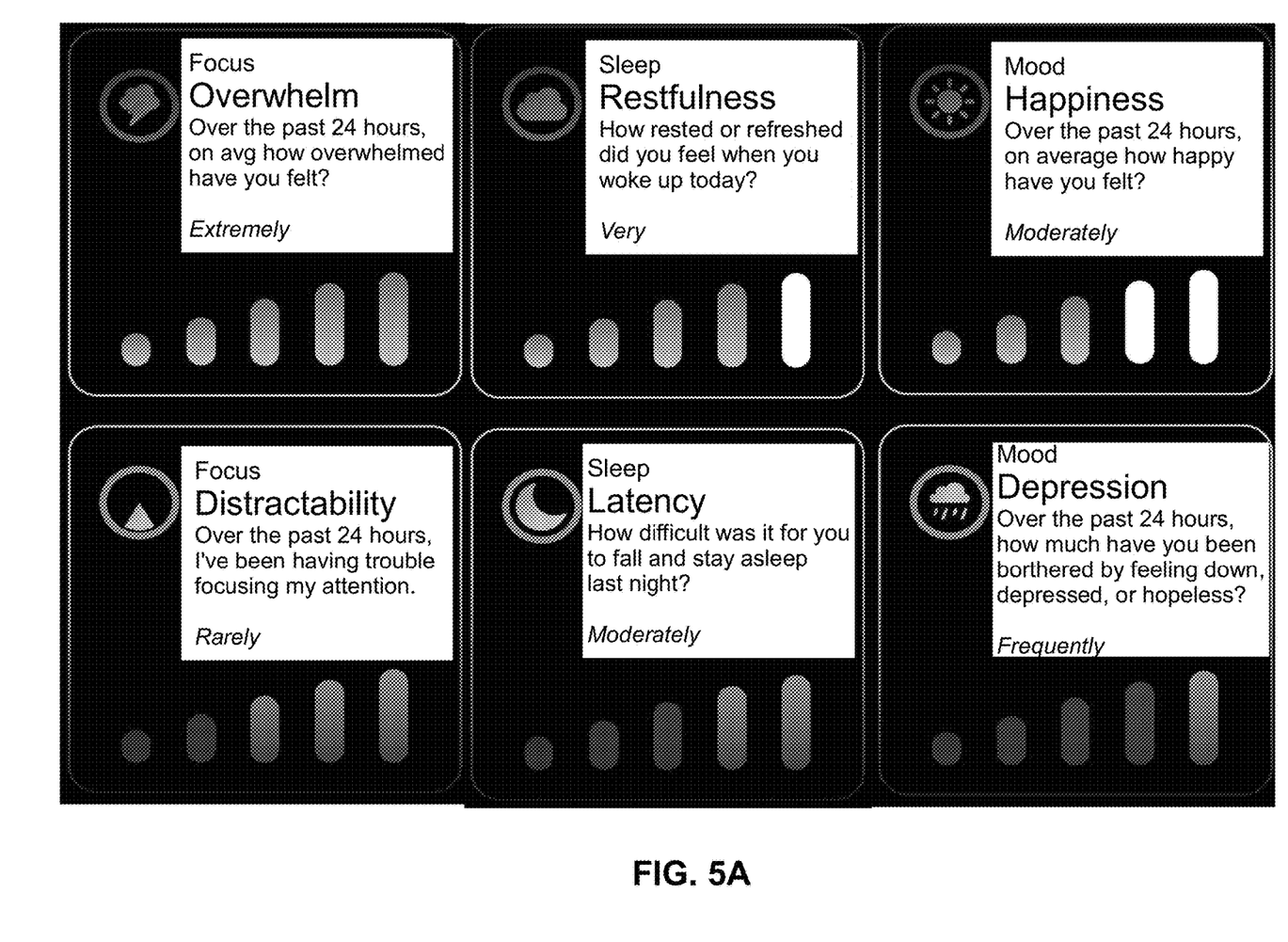
FIGS. 5A and 5B illustrate graphical user interfaces for a system for neurological training according to non-limiting embodiments or aspects.

Referring now to FIG. 5A, graphical user interfaces are shown with outcome queries for the user to respond to according to non-limiting embodiments. Such queries may be presented to the user to prompt the user for a response before a session, after a session, during a session, and/or at scheduled intervals (e.g., morning, evening, midday, and/or the like). For example, a user may be prompted for a response to one or more queries daily, weekly, and/or the like, and such prompts may be presented when an application is being executed, as push notifications, and/or the like. Such responses may be used to determine and display a user's progress over time, to customize one or more neurological training programs, and/or the like. As shown in the example in FIG. 5A, a user may provide a response from a range of possible responses (e.g., rarely, moderately, frequently, etc.). Responses may be numerical (e.g., where one end of the range represents a negative response and the other end of the range represents a positive response) and/or graphical (e.g., as shown in the bars of FIG. 5A). In some non-limiting embodiments the responses may be binary (e.g., yes or no). It will be appreciated that various forms of queries and responses may be used.

Figure 5B:
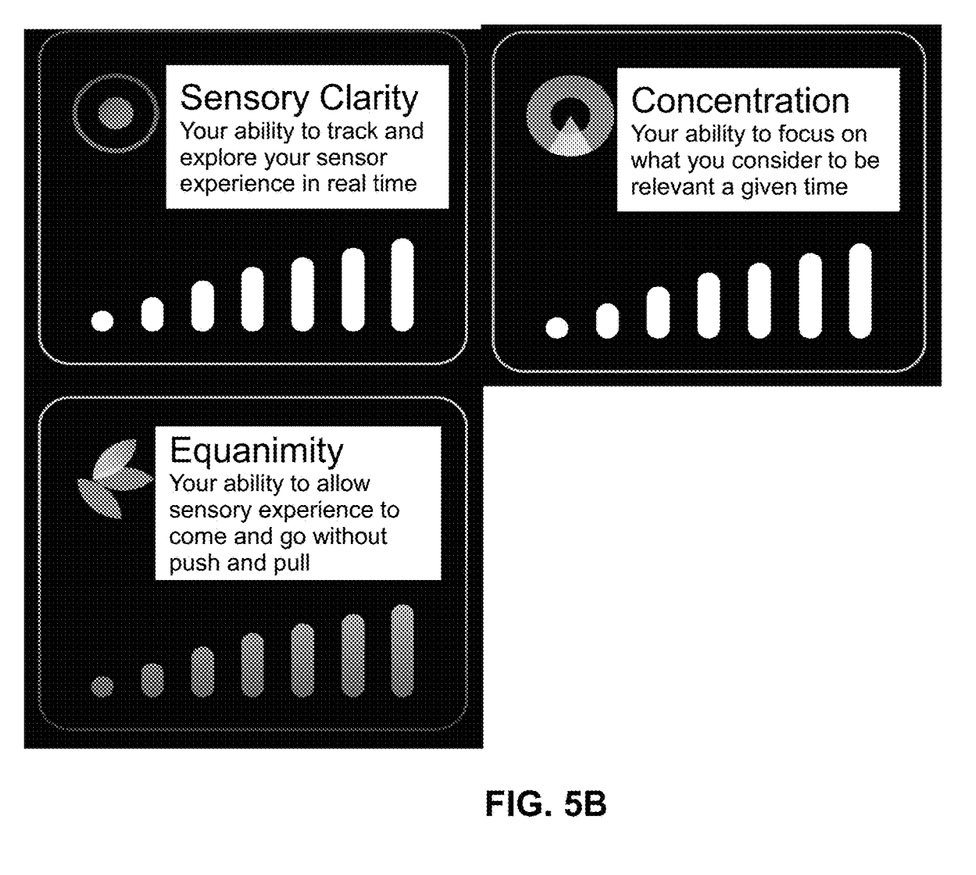

Referring now to FIG. 5B, graphical user interfaces are shown with skill development queries for the user to respond to according to non-limiting embodiments. Such queries may be presented to the user to prompt the user for a response before a session, after a session, during a session, and/or at scheduled intervals (e.g., morning, evening, mid-day, and/or the like). For example, a user may be prompted for a response to one or more queries daily, weekly, and/or the like, and such prompts may be presented when an application is being executed, as push notifications, and/or the like. Such responses may be used to determine and display a user's progress with respect to skill development over time, to customize one or more neurological training programs, to select a sequence of neurological training programs, and/or the like. As shown in the example in FIG. 5B, a user may be prompted to assess their concentration, sensory clarity, and equanimity. It will be appreciated that additional, fewer, or different queries may be presented to a user. Responses may be numerical (e.g., where one end of the range represents a negative response and the other end of the range represents a positive response) and/or graphical (e.g., as shown in the bars of FIG. 5B).

Figure 6:
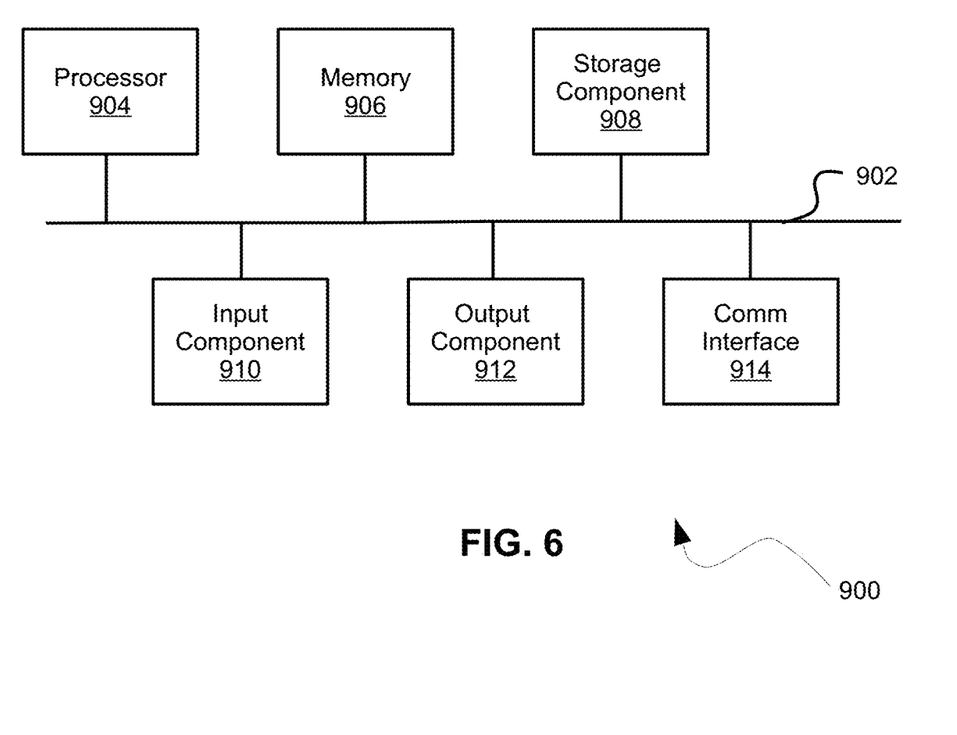
FIG. 6 illustrates example components of a computing device used in connection with non-limiting embodiments.

Referring now to FIG. 6, shown is a diagram of example components of a computing device 900 for implementing and performing the systems and methods described herein according to non-limiting embodiments. In some non-limiting embodiments, device 900 may include additional components, fewer components, different components, or differently arranged components than those shown. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 6, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A computer-implemented method for interactive neurological training, comprising:
    traversing, with at least one processor, a graph data structure based on a user profile for a user operating a device, the graph data structure comprising a plurality of nodes, each node of the plurality of nodes associated with at least one of a logical statement and an audible output;
    presenting at least one audible output to the user based on at least one node of the graph data structure;
    receiving a gesture input from the user through the device in response to the at least one audible output, the gesture input detected by at least one sensor arranged in the device;
    determining, based on the gesture input and at least one logical statement associated with the at least one node, a next node of the graph data structure from at least two different nodes connected to the at least one node; and
    presenting at least one further audible output to the user based on the next node of the graph data structure.

2. The computer-implemented method of claim 1, wherein the at least one sensor comprises a touchscreen, and wherein the gesture input comprises at least one press on the touchscreen.

3. The computer-implemented method of claim 1, wherein the at least one logical statement associated with the at least one node is configured to identify the next node based on the gesture input.

4. The computer-implemented method of claim 1, further comprising assigning weights to nodes of the graph data structure based on the user profile.

5. The computer-implemented method of claim 1, further comprising traversing the graph data structure based on at least one machine-learning algorithm.

6. The computer-implemented method of claim 5, further comprising training the machine-learning algorithm based on the gesture input.

7. The computer-implemented method of claim 1, wherein the at least one logical statement is configured to identify a node or branch of the graph data structure based on a plurality of different gesture inputs, and wherein the gesture input is selected from the plurality of different gesture inputs.

8. The computer-implemented method of claim 1, further comprising:
    determining if the gesture input was received within a predetermined time period from the at least one audible output; and
    in response to determining that the gesture input was received within the predetermined time period, determining the next node.

9. A system for interactive neurological training, comprising:
    at least one data storage device comprising at least one graph data structure; and
    at least one processor in communication with the at least one data storage device, the at least one processor programmed or configured to:
        traverse a graph data structure from the at least one graph data structure based on a user profile for a user operating a device, the graph data structure comprising a plurality of nodes, each node of the plurality of nodes associated with at least one of a logical statement and an audible output;
        present at least one audible output to the user based on at least one node of the graph data structure;
        receive a gesture input from the user through the device in response to the at least one audible output, the gesture input detected by at least one sensor arranged in the device;
        determine, based on the gesture input and at least one logical statement associated with the at least one node, a next node of the graph data structure from at least two different nodes connected to the at least one node; and
        present at least one further audible output to the user based on the next node of the graph data structure.

10. The system of claim 9, wherein the at least one sensor comprises a touchscreen, and wherein the gesture input comprises at least one press on the touchscreen.

11. The system of claim 9, wherein the at least one logical statement associated with the at least one node is configured to identify the next node based on the gesture input.

12. The system of claim 9, wherein the at least one processor is further configured to assign weights to nodes of the graph data structure based on the user profile.

13. The system of claim 9, wherein the at least one processor is further configured to traverse the graph data structure based on at least one machine-learning algorithm.

14. The system of claim 13, wherein the at least one processor is further configured to train the machine-learning algorithm based on the gesture input.

15. The system of claim 9, wherein the at least one logical statement is configured to identify a node or branch of the graph data structure based on a plurality of different gesture inputs, and wherein the gesture input is selected from the plurality of different gesture inputs.

16. The system of claim 9, wherein the at least one processor is further configured to:
    determine if the gesture input was received within a predetermined time period from the at least one audible output; and
    in response to determining that the gesture input was received within the predetermined time period, determine the next node.

17. A computer program product for interactive neurological training, comprising at least one non-transitory computer-readable medium including program instructions that, when executed by at least one processor, cause the at least one processor to: traverse a graph data structure based on a user profile for a user operating a device, the graph data structure comprising a plurality of nodes, each node of the plurality of nodes associated with at least one of a logical statement and an audible output; present at least one audible output to the user based on at least one node of the graph data structure; receive a gesture input from the user through the device in response to the at least one audible output, the gesture input detected by at least one sensor arranged in the device; determine, based on the gesture input and at least one logical statement associated with the at least one node, a next node of the graph data structure from at least two different nodes connected to the at least one node; and present at least one further audible output to the user based on the next node of the graph data structure.

* * * * *